United States Patent [19]

Pöhler

[11] Patent Number: 5,706,389
[45] Date of Patent: Jan. 6, 1998

[54] ELECTRICALLY HEATED HEAT EXCHANGER

[75] Inventor: Jörg Pöhler, Ronnenberg, Germany

[73] Assignee: Drägerwerk Aktiengesellschaft, Lübeck, Germany

[21] Appl. No.: 602,224

[22] Filed: Feb. 16, 1996

[30] Foreign Application Priority Data

Mar. 17, 1995 [DE] Germany ............ 195 09 772.6

[51] Int. Cl.[6] ............................................. F22B 29/06
[52] U.S. Cl. ..................................... 392/397; 392/480
[58] Field of Search .............................. 392/394, 396, 392/397, 400, 471, 480, 481; 420/469, 485, 487

[56] References Cited

U.S. PATENT DOCUMENTS

| | | |
|---|---|---|
| 1,557,044 | 10/1925 | Graham .............................. 420/487 |
| 2,086,140 | 7/1937 | Silten . |
| 3,234,357 | 2/1966 | Seuthe .............................. 392/403 |
| 3,964,604 | 6/1976 | Parrish .............................. 392/397 |
| 4,547,656 | 10/1985 | Swiatosz .......................... 392/397 |
| 4,558,196 | 12/1985 | Babasade ......................... 392/397 |
| 4,578,320 | 3/1986 | Mahulikar et al. .............. 420/487 |
| 4,764,660 | 8/1988 | Swiatosz .......................... 392/397 |
| 4,818,843 | 4/1989 | Swiatosz .......................... 392/397 |

Primary Examiner—Teresa J. Walberg
Assistant Examiner—Sam Paik
Attorney, Agent, or Firm—McGlew & Tuttle

[57] ABSTRACT

A device for evaporating liquids to generate fog has an electrically heated heat exchanger. A device and a process are provided, which make possible the rapid heating of the liquids to be evaporated to a predetermined temperature range. This is achieved by the wall of the heat exchanger being made of an electrically conducting material and being connected to an electric power source for direct heating.

8 Claims, 2 Drawing Sheets

5,706,389

ELECTRICALLY HEATED HEAT EXCHANGER

FIELD OF THE INVENTION

The present invention pertains to a device and a process for evaporating liquids in an electrically heated heat exchanger.

BACKGROUND OF THE INVENTION

Such a device has been known from U.S. Pat. No. 2,086,140. The prior-art device is used to evaporate anesthetics and comprises essentially a tube, which is bent in a helical shape and is surrounded by a temperature-controlled heating device.

The process according to the present invention is used in a device for generating fog according to the principle of evaporation. Such fogs are used, e.g., to make visible the movements of air, gases or vapors, or in film and stage technology. The liquids to be evaporated usually consist here of a mixture of alcohols and water. This mixture is pumped by means of a pump through a heat exchanger, whose temperature is maintained between 250° C. and 340° C.

The gases being discharged then generate fog due to condensation.

The usual heat exchangers are designed as follows:

A heat-storing mass (iron, aluminum, copper), in or on which the channels carrying the liquids to be evaporated are located, is heated by means of a resistance heating (heating cartridge, tubular heating element). The heat exchangers are permanently maintained at the evaporation temperature, which requires the continuous supply of heat. To reduce these heat losses, the heat exchangers are insulated with an insulating material (mineral wool, ceramic wool). On the whole, the ratio of the thermal capacity to the available heating capacity is high, which leads to heat-up times of 5 to 20 minutes. The spatial dimensions of a thermally insulated heat exchanger are between 800 mL and several L. The weight is between 400 g and a few kg.

SUMMARY AND OBJECTS OF THE INVENTION

The object of the present invention is to provide a device and a process for evaporating liquids, by which rapid heating of the liquids to be evaporated is made possible.

According to the invention, a device for evaporating liquids in an electrically heated heat exchanger is provided. The wall of the heat exchanger is made of an electrically conducting material and is connected to an electric power source for direct heating.

According to a further aspect of the invention, a process is provided for evaluating liquids employing an electrically heated heat exchanger wherein the wall of the heat exchanger is provided with electrically conducting material and is connected to the electric power source for direct heating. The heating current is controlled as a function of the current temperature of the heat exchanger.

At least one section of the heat exchanger is preferably designed as a heating resistor with low temperature coefficient and is used directly as a measuring resistor for measuring the temperature of the heat exchanger. The measuring resistor with an electronic evaluation unit connected in parallel is preferably arranged between the heat exchanger and the power source. The output of the electronic evaluation unit is connected directly to the power source.

The heat exchanger is preferably designed as a round tube with an internal diameter of between 0.3 to 1 mm. The wall thickness is preferably 0.1 to 0.3 mm and the length is preferably from 120 to 1,000 mm.

The process of the invention preferably further includes determining the current temperature of the heat exchanger section by section. This preferably entails measuring the electrical resistance. The heating current is also preferably controlled section by section as a function of the measured electrical resistance.

The essential advantage of the present invention is that a compact device for evaporating liquids is provided, which makes possible rapid heating directly for use, i.e., the ratio of the thermal capacity of the device to its heating capacity is low. It is possible as a result to reach the needed evaporation temperature in a very short time, so that heating of the heat exchanger is possible only during the fog generation process. This is a favorable prerequisite for mobile use, i.e., for nonsystem-connected operation. The compact design makes it possible to drastically reduce the weight and volume, so that new possibilities of application become practicable in the area of the miniaturization of fog generators and their direct introduction in test fields or poorly accessible sites of use.

The basic idea of the present invention is the direct electrical heating of the heat exchanger, and the heat exchanger itself is preferably used as a measuring sensor for its temperature, and deviations in the heating temperature or heating current are controlled extremely rapidly by means of a suitable electronic evaluation unit as a function of corresponding measured signals. This is especially desirable for the evaporation of fog fluids, because it takes place in a relatively narrow temperature range: If the temperature is too low, the fog fluid discharged is still liquid or only partially evaporated. Components of the fluid are thermally destroyed if the temperature is too high, and products which are hygienically undesirable may be formed. Temperature sensors, which follow the temperature to be measured only after a certain response time, depending on their design and size and have an additional thermal capacity themselves, are usually used.

Any change in temperature is detected according to the present invention as a change in resistance without any time delay, and no additional masses to be heated, in the form of sensors, are necessary.

Two embodiments of the present invention are described with reference to the two figures.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
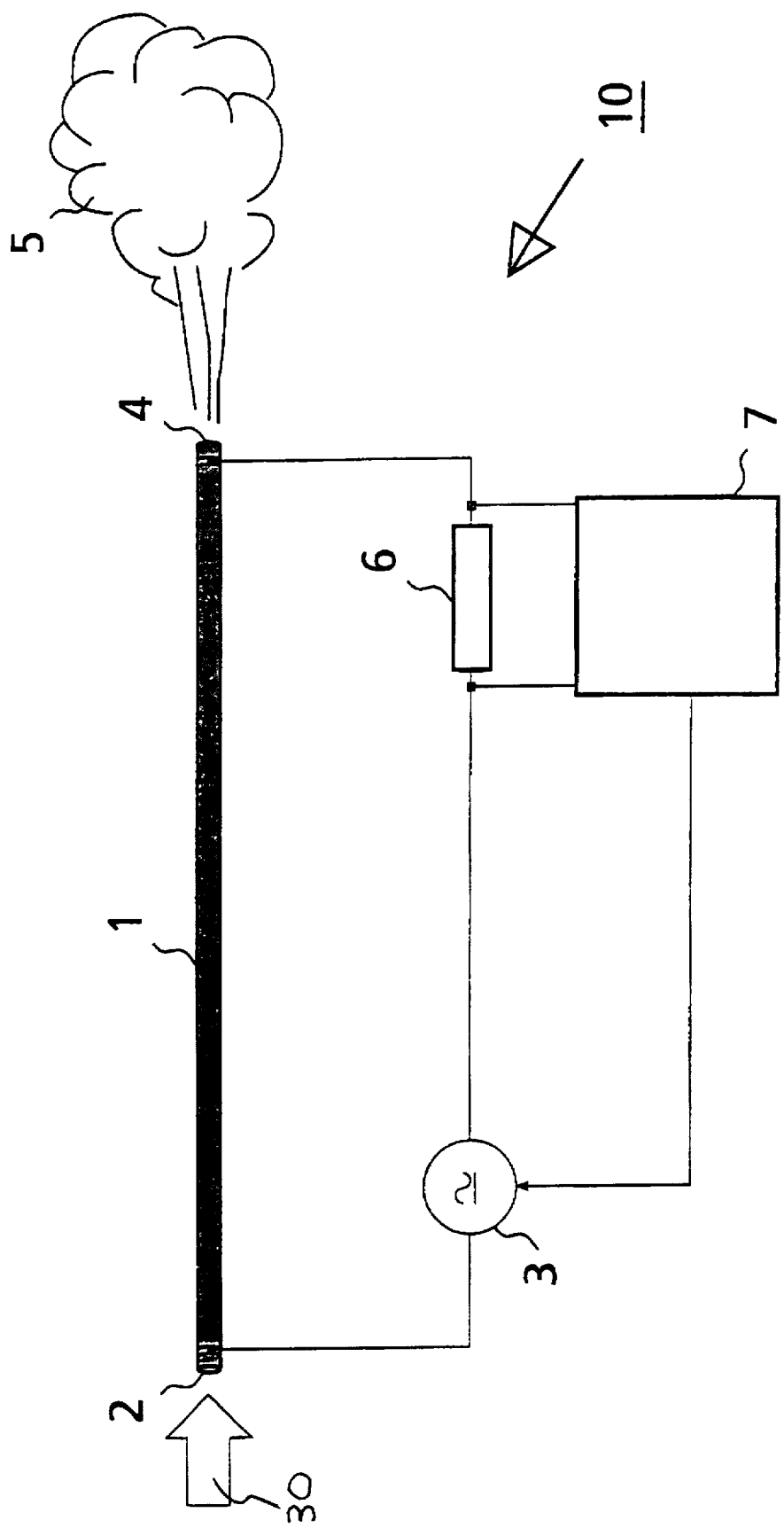
FIG. 1 is a schematic view showing the basic structure of a device according to the present invention.

In the structure 10 according to FIG. 1, the fog fluid to be evaporated is introduced into a thin-walled metal tube 1 through the inlet opening 2 in the direction of the arrow 30, e.g., by means of a reciprocating pump from a reservoir. However, other types of delivery, e.g., with compressed air or by gravity, are also conceivable. The material of the tube preferably comprises stainless steel, but other, electrically conducting materials may be used as well.

The current supplied by the power source 3 heats the metal tube 1, and the evaporated fog fluid discharged through the opening 4 forms a fog cloud 5 after condensation. The current flowing through the thin-walled metal tube 1 and the measuring resistor 6 results in a voltage drop over the measuring resistor 6, and this voltage drop is measured in an electronic control unit (evaluation unit) 7 and is used to control the power source 3.

Depending on the temperature coefficient of the tube material, a defined temperature of the tube 1 can be assigned to the voltage drop on the measuring resistor 6. The electronic control unit 7 can thus adjust the current through the metal tube 1 to a value that is necessary for reaching a desired temperature for the evaporation of the fog fluid. Corresponding to this basic structure shown in FIG. 1, it is also conceivable to divide the metal tube 1 into separately controlled areas. More uniform heating over the length can take place in this case, because individual sections of the tube 1 are electrically heated, measured, and controlled.

The metal tube 1 has an internal diameter between 0.3 and 1 mm, a wall thickness between 0.1 and 0.3 mm, and a length of 120 to 1,000 mm.

Figure 2:
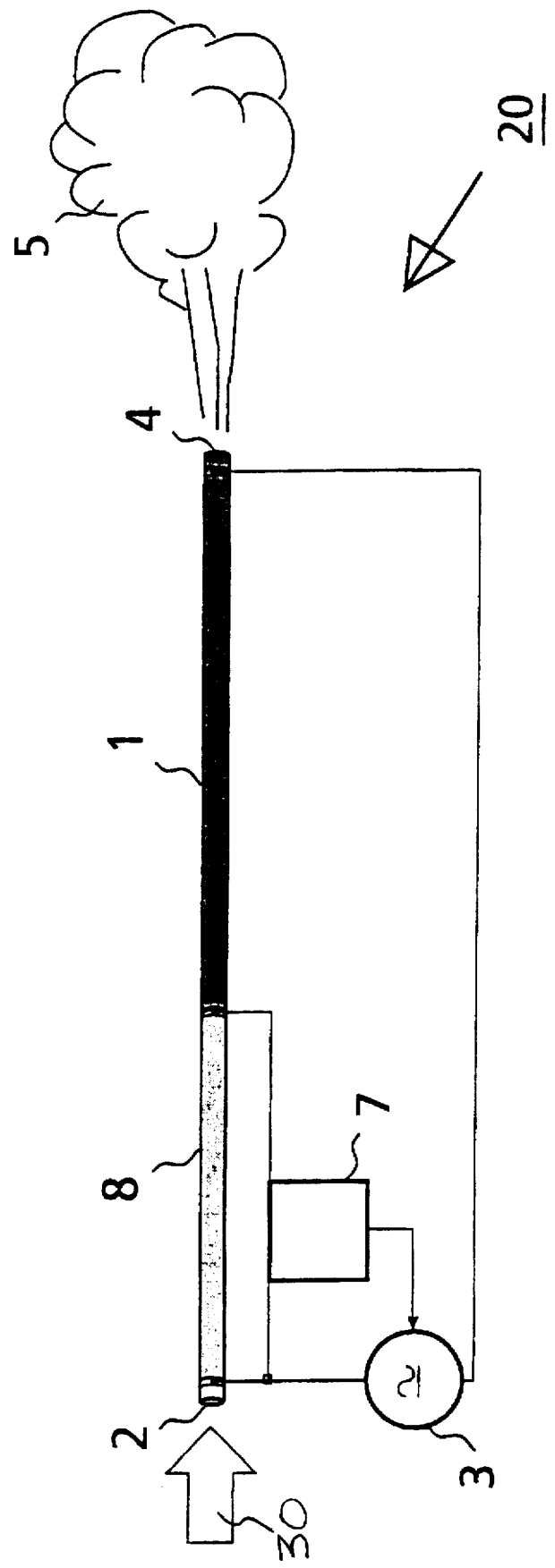
FIG. 2 is a view similar to FIG. 2 showing the design of a variant of the present invention.

The variant 20 according to FIG. 2 shows a design of a tube section 8 as a heating resistor with very low temperature coefficient, the material of the tube section 8 is made of, e.g., constantan. This offers the advantage that the marked tube section 8 can be directly used as a measuring resistor, monitored by electronic control unit 7. The consequence of this is that the heat due to energy loss on the measuring resistor can be used to heat the fluid and a relatively high measuring voltage can be selected, which simplifies and optimizes the evaluation circuit.

The tube section 8 made of constantan, an alloy of about 55% copper and 45% nickel. In the embodiment of FIG. 2, the remainder of the heat exchanger is formed of stainless steel.

While specific embodiments of the invention have been shown and described in detail to illustrate the application of the principles of the invention, it will be understood that the invention may be embodied otherwise without departing from such principles.

What is claimed is:

1. A device for evaporating liquids, comprising:

an electrically heated heat exchanger with a liquid inlet and an evaporated liquid outlet, said heat exchanger including a wall made of an electrically conducting material;

a power source connected to said wall for direct heating; and an evaluation unit and a measuring resistor wherein said measuring resistor with said electronic evaluation unit connected in parallel is arranged electrically connected between said heat exchanger and said power source, and an output of the said electronic evaluation unit is connected directly to said power source.

2. A device for evaporating liquids in accordance with claim 1, wherein said heat exchanger is a round tube with an internal diameter of 0.3 to 1 mm, and said wall has a thickness of 0.1 to 0.3 mm, and a length of 120 to 1,000 mm.

3. A process for evaluating liquids with a device with an electrically heated heat exchanger with a liquid inlet and an evaporated liquid outlet, said heat exchanger including a wall made of an electrically conducting material and a power source connected to said wall for direct heating, the process comprising the steps of:

providing an evaluation unit and a measuring resistor wherein said measuring resistor with said electronic evaluation unit connected in parallel is arranged electrically connected between said heat exchanger and said power source, and an output of the said electronic evaluation unit is connected directly to said power source;

determining the heating current, which is a function of the current temperature of said heat exchanger by measuring the voltage across said measuring resistor; and adjusting said heating current with said evaluation unit to attain a desired temperature of said heat exchanger.

4. A process for evaporating liquids in accordance with claim 3, wherein the current temperature of said heat exchanger is determined section by section by measuring the electrical resistance, and that the heating current is also controlled section by section as a function of the measured electrical resistance.

5. A device for evaporating liquids, comprising:

a heat exchanger with a liquid inlet and an evaporated liquid outlet, said heat exchanger including a wall made of an electrically conducting material and including at least one low temperature coefficient section of said heat exchanger designed as a heating resistor, said heat exchanger including a remaining section having a temperature coefficient higher than said low temperature coefficient section;

a power source connected to said wall for direct heating of said wall; and control means connected to said wall for regulating the temperature of said wall by adjusting electrical current flowing therethrough, said low temperature coefficient section of said heat exchanger being electrically connected directly to said control means as a measuring resistor for measuring changes in voltage across said low temperature coefficient section to provide a measurement of the temperature of said heat exchanger.

6. A device for evaporating liquids in accordance with claim 5, wherein said at least one section is formed of an alloy of about 55% copper and about 45% nickel and a remainder of said heat exchanger is formed of stainless steel.

7. A device for evaporating liquids in accordance with claim 5, wherein said heat exchanger is a round tube with an internal diameter of 0.3 to 1 mm, and said wall has a thickness of 0.1 to 0.3 mm, and a length of 120 to 1,000 mm.

8. A process for evaluating liquids with a device with an electrically heated heat exchanger with a liquid inlet and an evaporated liquid outlet, said heat exchanger including a wall made of an electrically conducting material and a power source connected to said wall for direct heating, the process comprising the steps of:

providing the heat exchanger with at least one low temperature coefficient section as a measuring resistor and a remaining section having a temperature coefficient higher than said low temperature coefficient section;

providing an evaluation unit;

measuring changes in voltage across said low temperature coefficient section with said evaluation unit to determine the heating current through said heat exchanger, which is a function of the current temperature of said remaining section of said heat exchanger; and adjusting said heating current with said evaluation unit to attain a desired temperature of said heat exchanger.

* * * * *